United States Patent
Rodinger et al.

(10) Patent No.: US 9,165,052 B2
(45) Date of Patent: Oct. 20, 2015

(54) DENSITY BASED CLUSTERING FOR MULTIDIMENSIONAL DATA

(75) Inventors: Tomas Rodinger, Vancouver (CA); Paula L. Lario, Vancouver (CA)

(73) Assignee: ZYMEWORKS INC., Vancouver (CA)

(*) Notice: Subject to any disclaimer, the term of this patent is extended or adjusted under 35 U.S.C. 154(b) by 732 days.

(21) Appl. No.: 13/511,523

(22) PCT Filed: Nov. 23, 2010

(86) PCT No.: PCT/CA2010/001873
§ 371 (c)(1),
(2), (4) Date: Sep. 14, 2012

(87) PCT Pub. No.: WO2011/063518
PCT Pub. Date: Jun. 3, 2011

(65) Prior Publication Data
US 2013/0013631 A1    Jan. 10, 2013

Related U.S. Application Data

(60) Provisional application No. 61/264,196, filed on Nov. 24, 2009.

(51) Int. Cl.
*G06F 17/30* (2006.01)
*G06F 19/24* (2011.01)
*G06F 19/18* (2011.01)

(52) U.S. Cl.
CPC .... *G06F 17/30598* (2013.01); *G06F 17/30657* (2013.01); *G06F 17/30867* (2013.01); *G06F 19/24* (2013.01); *G06F 19/18* (2013.01)

(58) Field of Classification Search
CPC ............... G06F 17/30598; G06F 17/30657; G06F 17/30867
USPC ................. 707/769, 770; 706/62
See application file for complete search history.

(56) References Cited

U.S. PATENT DOCUMENTS

| | | | |
|---|---|---|---|
| 6,226,408 B1 | 5/2001 | Sirosh | |
| 2003/0142094 A1 | 7/2003 | Zhang | |
| 2009/0043220 A1 | 2/2009 | Montgomery et al. | |

FOREIGN PATENT DOCUMENTS

WO    WO 01/16880    5/2001

OTHER PUBLICATIONS

Keisuke Sakurai, et al., "Online Semi-Supervised Active Learning Method Using Competitive Neural Network", Journal of IEICE (J90-D), vol. 11, Japan, The Institute of Electronics, Information and Communication Engineers (IEICE), Nov. 1, 2007, pp. 3091-3102.

(Continued)

*Primary Examiner* — Shahid Alam
(74) *Attorney, Agent, or Firm* — Morgan, Lewis & Bockius LLP; Brett Lovejoy

(57) ABSTRACT

A new density based clustering method for clustering data points in multidimensional space is described. Each point has a neighborhood consisting of all points that are within a preset cutoff radius or distance. Each point is assigned a density measure based on the number of points in its neighborhood. Any point that has a higher density than any of its neighboring points is the center of a cluster and is assigned a unique cluster ID. Every other point follows a path through the graph of neighboring points such that density is increasing as fast as possible until a cluster center is reached. The algorithm's performance is demonstrated on a one-dimensional, two-dimensional, and 18-dimensional dataset.

20 Claims, 6 Drawing Sheets

(56) References Cited

OTHER PUBLICATIONS

Shen Furao, Keisuke Sakurai, Youki Kamiya and Osamu Hasegawa: "An Online Semi-supervised Active Learning Algorithm with Self-organizing Incremental Neural Network," The 2007 International Joint Conference on Neural Network (IJCNN 2007), Orlando, FL, USA, Aug. 2007.

Agrawal et al., "Automatic Subspace Clustering of High Dimensional Data for Data Mining Applications" IBM Almaden Research Center (1998).

Ankerst et al., "OPTICS: Ordering Points to Identify the Clustering Structure" *Proceedings of the 1999 SIGMOD International Conference on Management of Data*, pp. 49-60, Institute for Computer Science, University of Munich (1999).

Daura et al., "Peptide Folding: When Simulation Meets Experiment" *Agnew. Chem. Int. Ed.* vol. 38. No. 1/2, pp. 236-240 (1999).

Ester et al., "A Density-Based Algorithm for Discovering Clusters in Large Spatial Databases with Noise" *Proceedings of the Second International Conference on Knowledge and Discovery and Data Mining*, pp. 226-231 (1996).

Fahim et al., "DCBOR: A Density Clustering Based on Outlier Removal" *World Academy of Science, Engineering and Technology*, vol. 35 (2008).

Fu, et al., "Flame, a novel fuzzy clustering method for the analysis of DNA microarray data" *BMC Bioinformatics*, vol. 8, No. 3, pp. 1-15 (2007).

Hartigan et al., "A *K*-Means Clustering Algorithm" *Journal of the Royal Statistical Society, Series C (Applied Statistics)*, vol. 28, No. 1, pp. 100-108, Wiley-Blackwell (1979).

Hinneburg et al., "An Efficient Approach to Clustering in Large Multimedia Databases with Noise", Institute of Computer Science, University of Halle Germany (1998).

Kailing et al., "Density-Connected Subspace Clustering for High-Dimensional Data", *Proceedings of the SIAM Int. Conf on Data Mining*, pp. 246-257, Institute for Computer Science, University of Munich, Germany (2004).

Zong et al., "A New Clustering Algorithm of Large Datasets with O(N) Computational Complexity", *IEEE Transactions on Neural Networks*, vol. 10, No. 1 (1999).

DENSITY BASED CLUSTERING FOR MULTIDIMENSIONAL DATA

CROSS-REFERENCE TO RELATED APPLICATIONS

This application claims under 35 USC 119(e) the benefit of U.S. Application 61/264,196, filed Nov. 24, 2009, which is incorporated by reference in its entirety.

TECHNICAL FIELD

The invention relates to the field of chemical modeling and design.

BACKGROUND

The volume and types of data produced by biological science and theoretical chemistry are vast. Such fields as protein conformation, chemical and protein structure and activity; genomic sequences, gene expression and phenotype; and population and disease incidence and prevalence yield large amounts of interrelated data that must be organized and interpreted to be useful.

A variety of methods have been designed to "cluster", or organize, large amounts of technical data, including that relating to three-dimensional molecular forms.

Algorithms are used to perform the enormous number of decision-making steps required to organize shape data. Examples include: "DBSCAN", proposed by Martin Ester, Hans-Peter Kriegel, Jörg Sander, Xiaowei Xu in Proceedings of the Second International Conference on Knowledge Discovery and Data Mining (KDD-96): 226-231, in 1996; "OPTICS", proposed by M. Ankerst et al. Proc. ACM SIG-MOI'99 Int. Conf. on Management of Data, Philadelphia Pa., 1999; "K-means", proposed by J. A. Hartigan et al in "A K-Means Clustering Algorithm". Applied Statistics 28 (1): 100-108, 1979; "K-medoid", referenced at http://en.wikipedia.org/wiki/K-medoids; "FLAME" proposed by L. Fu et al. in BMC Bioinformatics 2007, 8:3, 2007; "G_cluster/grooms" proposed by Daura et al. in Angew. Chem. Int. Ed. 1999, 38, pp 236-240, 1999; "DCBOR", proposed by A. M. Fahim, G. Saake, A. M. Salem, F. A. Torkeyand, M. A. Ramadan. in Proceedings of World Academy of Science, Engineering and Technology, Vol. 35, November 2008; "DENCLUE", proposed by Alexander Hinneburg and Daniel A Keim in An Efficient Approach to Clustering in Large Multimedia Databases with Noise. Institute of Computer Science University of Halle Germany, 1998; "SUBCLU", Karin Kailing, Hans-Peter Kriegel and Peer Kroger In Proc. SIAM Int. Conf. on Data Mining (SDM'04), pp. 246-257, 200, 2004; and CLIQUE, proposed by Rakesh Agrawal, Johannes Gehrke, Dimitrios Gunopulos, and Prabhakar Raghavan of IBM Almaden Research Center, 1998.

These methods have various limitations, such as being unable to cluster data with varying densities across a volume, yielding inconsistent results depending on the input order, producing clusters based on shape and not density, or being confined to smaller datasets. Of these, FLAME and DEN-CLUE share the advantage of having only one required parameter and defining arbitrarily-shaped clusters.

The FLAME algorithm starts with a neighborhood graph to connect each data point to its K-nearest neighbors, estimates a density for each object based on its proximities to its K-nearest neighbors, and any data point with a density higher than all its neighbors is assigned full membership to itself. Remaining data points are assigned equal membership weights to all clusters defined, and then membership weights are updated for all points as a linear combination of the membership weights of its neighbors. This process is iterated to convergence, whereupon each object is assigned to the cluster in which it has the highest membership. FLAME needs many iterations and is inefficient and time consuming.

In DENCLUE, each data point is assigned an influence function that determines the effect of itself on the surrounding areas. A typical influence function can be a Gaussian distribution centered around the point. The algorithm sums together the influence functions of all points and then proceeds to find local maxima on this new hypersurface. Cluster centers are located at these maxima. The cluster to which points belong is found via a steepest ascent procedure on this hypersurface. An efficient implementation of this algorithm is very complex.

U.S. Pat. No. 6,226,408 by Sirosh discloses an unsupervised learning routine for use in analyzing credit card transactions for fraudulent activity. A number of data types are converted to numerical values and grouped accordingly.

SUMMARY OF INVENTION

In one aspect, the invention provides a method of clustering a first query datapoint to a first cluster comprising a first cluster center, wherein the first query datapoint and the first cluster center are selected from a plurality of datapoints in space and wherein each of the datapoints is characterized by a density, the method comprising (a) determining a first trace of the first query datapoint to the first cluster center, wherein the first trace comprises n datapoints selected from the plurality of datapoints and wherein n is an integer, the determining step comprising: (i) designating the first query datapoint as $x_1$; (ii) determining the remaining n−1 datapoints of the first trace, wherein the remaining n−1 datapoints are designated $x_2 \ldots x_n$; wherein $x_n$ designates the first cluster center; and wherein $x_{j+1}$ has the greatest density of all datapoints lying within a cutoff distance from $x_j$, wherein j is an integer selected from 1 to n−1; and (b) assigning the first query datapoint to the first cluster.

The methods of the invention advantageously are density based and do not force a particular shape on clusters. The methods have only one adjustable parameter (preset radius or cutoff distance) and are therefore easy to optimize. The methods further do not presuppose any particular number of clusters, which is determined by the algorithm and does not need to be specified. Additional qualities of the methods include noise tolerance and faster execution than other (more complicated) algorithms. That is, the methods are not adversely affected by noise and are fast compared to other more complicated algorithms. Furthermore, the methods can form clusters of varying densities separated by varying lower density regions.

The methods of the invention are useful for grouping large amounts of quantitative data into meaningful categories. The methods achieve their goal without using an iterative procedure of a type commonly performed in the literature. This substantially reduces the processing time required and allows them to be run on practical computing systems.

BRIEF DESCRIPTION OF DRAWINGS

FIG. 5 represents FIG. 4 viewed in the direction of the psi angle axis. Thus, in FIG. 5, the x-axis represents the phi angle and the y-axis represents density.

DESCRIPTION OF EMBODIMENTS

Figure 1:
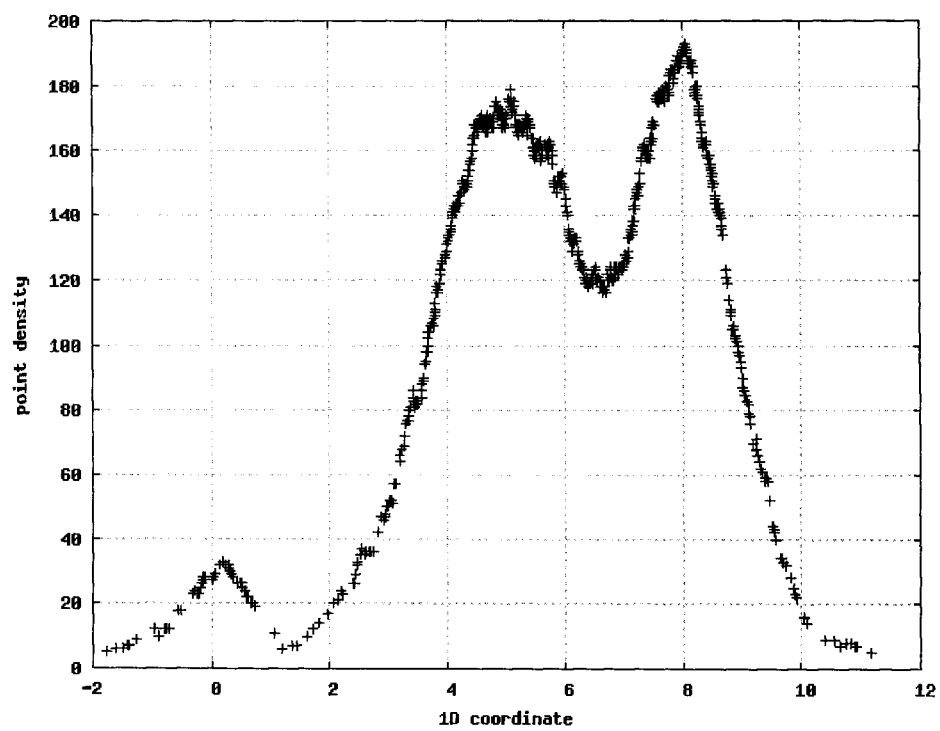
FIG. 1 shows a one-dimensional (1D) data set. The density of each point is plotted against the point's 1D coordinate value.

The present invention provides methods of data analysis useful in a wide variety of applications. These methods comprise grouping the datapoints of a dataset comprising a plurality of datapoints in space into one or more subsets or "clusters" as discussed below.

In one aspect, the invention provides a method of clustering a first query datapoint to a first cluster comprising a first cluster center, wherein the first query datapoint and the first cluster center are selected from a plurality of datapoints in space and wherein each of the datapoints is characterized by a density.

"Datapoint" in this application is taken to mean an association of one or more one-dimensional measurable quantities. Typically, these quantities are related or correlated in some meaningful and interesting way. An example would include groupings such as x, y, and z coordinates that describe the position of an object, phi/psi angles that describe the conformation of a protein, protein configuration and protein activity, nucleic acid expression levels and phenotype, or any other combination of measurements. Generally, a datapoint can refer to a set of measured quantities.

"Cluster" refers to a set of datapoints or observations that are grouped into a subset. Datapoints or observations in the same cluster are typically similar in some sense. Clustering is a technique for statistical data analysis referenced in many fields, including data mining, machine learning, pattern recognition, image analysis and bioinformatics. As described below, a cluster is typically characterized by at least one datapoint, known as a "cluster center". The methods herein describe ways of assigning various datapoints of a given dataset into one or more clusters.

"Density" is a measure of how many datapoints occupy a given space. A 2-dimensional area or 3-dimensional volume having 100 datapoints is more dense than one of equal size containing 10 datapoints, for example. It will be understood by one of skill in the art that the dimensionality of the space is determined by the dimensionality of the datapoints of a given dataset. A space can be a 1, 2, 3, 4 or higher dimensional space.

The density of a datapoint is determined with reference to a threshold, known as a "preset radius", "cutoff" or "cutoff distance" (used interchangeably). The cutoff distance is a measure used to define the boundary around a given datapoint within which another datapoint needs to occur to be considered a neighbor. The density of a datapoint can thus refer to the number of all datapoints lying within a cutoff distance from the datapoint. One of skill in the art will appreciate that the cutoff distance is a generalized parameter that can be determined for a space of any dimensionality.

The cutoff distance must be established by the user in advance. This parameter plays a direct role in how the algorithm smoothes out noise and thus how many clusters it ultimately detects. A larger value leads to more smoothing and the datapoints will be grouped into fewer clusters. Setting a smaller value will result in more clusters. The cutoff distance should be set just high enough to deal with the noise but not so high so as to cause legitimately separate clusters to be incorrectly merged. The cutoff distance is a quantity greater than zero with units of the same type as the datapoints (distance, for example). The cutoff distance can be easily adjusted and optimized by the user according to the application at hand and the quality of the dataset.

"Noise" is taken to mean any form of random addition, statistical noise, measurement inaccuracy, or other unexplained variation or source of error in the datapoint quantities. Noise usually shows up as sporadically distributed points on a plot, local inconsistencies in point density, or high frequency fluctuation in otherwise slowly changing data. Noise makes the identification of the correct locations of local maxima and minima in a dataset difficult and this often confuses clustering algorithms.

In one embodiment, the method comprises (a) determining a first trace of the first query datapoint to the first cluster center, wherein the first trace comprises n datapoints selected from the plurality of datapoints and wherein n is an integer; and (b) assigning the first query datapoint to the first cluster. Thus, in this embodiment, assigning a point to a cluster can be conceptualized as determining a trace of the point to the cluster center of the cluster. A "trace" refers to a set of datapoints comprising a query datapoint, a cluster center and optionally one or more datapoints. Typically, each datapoint of the trace is characterized by some relationship to another datapoint in the trace, as discussed below.

Each point of the trace can be referred to using a trace index, i.e., each point of the trace can be designated $x_1$, $x_2$ and so on. The first point of the trace can be referred to as a "query" datapoint, labeled $x_1$. The query datapoint is a datapoint chosen by a practitioner to be related to some "cluster center". The relationship may be in reference to the density of the cluster center and of other datapoints. The relationship between the query datapoint and the cluster center may be direct, i.e., the cluster center may have the greatest density of all datapoints lying within a cutoff distance of the query datapoint. The relationship may be indirect, i.e., the cluster center may have the greatest density of all datapoints lying within a cutoff distance of an intermediate datapoint of the trace, which itself has the greatest density of all datapoints lying within a cutoff distance of the query datapoint. This indirect relationship can extend to any number of intermediate datapoints. Thus, in one embodiment, the step of determining a first trace of the first query datapoint to the first cluster center comprises (i) designating the first query datapoint as $x_1$; and (ii) determining the remaining n−1 datapoints of the first trace, wherein the remaining n−1 datapoints are designated $x_2 \ldots x_n$; wherein $x_n$ designates the first cluster center; and wherein $x_{j+1}$ has the greatest density of all datapoints lying within a cutoff distance from $x_j$, wherein j is an integer selected from 1 to n−1.

In one embodiment, no point within the cutoff distance from the first cluster center is characterized by a density higher than the density of the first cluster center.

Each point of the first trace could, in some other embodiment, be selected as a query datapoint. The trace of the query datapoint in these other embodiments would be a subset of the first trace that would include the first cluster center. Accordingly, in one embodiment, $x_1 \ldots x_n$ are all assigned to the first cluster.

In one embodiment, the density of $x_j$ or $x_{j+1}$ is the number of all datapoints selected from the plurality of datapoints whose distance to $x_j$ or $x_{j+1}$, respectively, is less than or equal to the cutoff distance.

In one embodiment, $x_2$ is the first cluster center. In other words, in one embodiment, a trace can consist of a query datapoint and a cluster center.

Each point of a trace can be determined sequentially starting from the first query datapoint $x_1$. The next datapoint, $x_2$, would have the greatest density of all datapoints lying with a cutoff distance of $x_1$. $x_2$ could thus be referred to as the local density maximum neighbor of $x_1$. If $x_2$ is not a cluster center, then the local density maximum neighbor of $x_2$ can be determined. This process is continued until a cluster center is determined. Thus, in one embodiment, the step of determining the remaining n−1 datapoints comprises determining a local density maximum neighbor of each of the datapoints of the first trace in sequence according to ascending index, wherein the local density maximum neighbor of $x_j$ is $x_{j+1}$.

The methods described herein may provide an ordered set of points from a given dataset. Thus, in one embodiment, the density of $x_{j+}$, is greater than the density of $x_j$.

In some instances, more than one datapoint may have the same highest density within the cutoff of a given point. In order to resolve this situation, a global index is assigned to each datapoint of the plurality of datapoints in space. The datapoint that is chosen to be assigned to the trace is the datapoint with the highest global index. The one or more rejected datapoints will have a global index that is lower than the global index of the point assigned to the trace. Thus, in one embodiment, the step of determining the remaining n−1 datapoints of the first trace further comprises rejecting a datapoint selected from the plurality of datapoints, wherein the density of one of the remaining n−1 datapoints $X_j$ and the density of the rejected datapoint are the same; wherein $X_i$ is characterized by a first global index, the rejected datapoint is characterized by a second global index and the first global index is greater than the second global index.

Each of the clusters determined for a given plurality of datapoints can be thought of as comprising more than one trace of datapoints. In other words, a number of different traces can be determined to lead to the same cluster center. Thus, in one embodiment, the method further comprises determining a second trace of a second query datapoint to the first cluster center; and assigning the second query datapoint to the first cluster. In one embodiment, the method further comprises assigning each datapoint of the second trace to the first cluster.

As discussed above, more than one cluster can be determined for a given plurality of datapoints. Each of the clusters will comprise its own cluster center and can be numbered. Thus, in one embodiment, the method further comprises clustering a second query datapoint to a second cluster comprising a second cluster center, numbering the first cluster, and numbering the second cluster.

In one embodiment, the cluster numbering and datapoint assignments to the first cluster and the second cluster are visualized by a computer-generated graph.

In one embodiment, the first cluster and the second cluster are visualized in two or three dimensions.

In one embodiment, the cutoff distance is a single tunable parameter that affects the ability of the algorithm to overcome noisy points scattered between the first cluster and a second cluster. In one embodiment, the cutoff distance is a parameter tuned such that the algorithm overcomes noisy points scattered between the first cluster and a second cluster.

The clustering methods described herein can be conceptualized and described in a number of different ways. In one aspect, a method is provided for dividing a plurality of datapoints into clusters according to density of the datapoints, the method including the steps of: a) for a datapoint arbitrarily selected, identifying all neighboring datapoints within a preset radius; b) counting the number of neighboring points within said radius and calling this the density at that datapoint; c) iterating steps a through b to compute the density for all datapoints; and then d) for a datapoint arbitrarily selected from the plurality of datapoints, finding the neighboring datapoint within the preset radius that has the highest density; e) for that higher-density datapoint, finding its neighboring datapoint with the highest density; f) iterating steps d to e until a datapoint is found that has no neighbors with a higher density than itself, and labelling this datapoint the centre of a cluster; g) assigning the original datapoint of step d to this cluster, and h) repeating steps d through g until all datapoints are assigned to a cluster.

As discussed above, the datapoints can represent basically any combination of phenomena that can be measured.

In one embodiment, the plurality of datapoints exist in a one-, two-, three-, or any higher dimensional space.

In one embodiment, the plurality of datapoints represent quantifiable phenomena selected from the group consisting of amino acid configurations, protein conformation coordinates, measurable differences between proteins, nucleic acid expression levels and phenotypic qualities.

"Measurable protein differences" or "measurable differences between proteins" refer to differences in a measured quantity with respect to a protein and can include different column retention times (different chromatography columns work by size exclusion, affinity, charge, etc.); physical property differences as measured by biophysical methods such as mass spectrometry, circular dichroism, fluorescence, phosphorescence, or standard spectroscopy techniques (different wavelengths measure different properties: visible, ultraviolet and infrared). Any method that can provide a number associated with a physical property can be used to generate a metric for clustering, as long as the property is normalized in such a way that a "cutoff parameter" or "cutoff distance" chosen will resolve the differences in that metric (to some extent, full resolution is not required as multi-dimensional clustering will resolve things).

Applications of the present methods include chemical modelling to improve therapeutic activity of proteins, chemical modelling to study pathological forms, optimizing nucleic acid or small molecule therapeutics, agricultural, or other biological purpose, associating chemical analysis with activity readouts, protein activity and structure correlation, bacterial flora profiling and health diagnoses and genomic sequence and expression data interpretation.

In one embodiment, an experimentally-derived protein structure may be simulated via computer algorithms to derive a theoretical trajectory that reveals atomic motions over time. An enormous quantity of data is produced to reflect the different theoretical positions of various atoms and bond angles. Time snapshots from this trajectory can be used to determine the possible protein "states". The method of the invention is used to process the different positions or datapoints into clusters of most-preferred and distinct states.

In another embodiment, a trajectory representing the time evolution of a protein, movement between conformational states can be analysed for each amino acid individually. Various metrics can be defined such as dihedral angles, angles between two bonds, angles between two planes (where each plane is defined by three atoms), and distances between atoms. These metrics separately or in any combination form the datapoints which are subsequently clustered using the methods of the invention. Each cluster then defines a distinct state of the amino acid. Having enumerated the states, it now becomes possible to find correlations and concerted movement of multiple amino acids as they transition from state to state.

In one embodiment of the invention, chromatography data can be organized and interpreted. For example, molecular weight, fluorescence, particle size, charged surface area, hydrodynamic radius, and tumbling rate are all properties that can be used for the clustering and separation of different proteins, protein isoforms, protein structural states, and proteins with different posttranslational modifications. The chromatographical data can be clustered to provide meaningful information. For example, runoff from a column may be chronologically plated in a multiwall plate and analysed by mass spectrometer, generating size data, and then an activity assay could be run on the same plated solutions to yield activity data for each well. The three dimensional data generated would then be analyzed using the methods of the invention to provide a structure-mass-activity relationship clustering.

In yet another embodiment, the invention can be used to cluster protein-protein interaction data. For example, proteins can be categorized based on differences in binding constants to other proteins.

In some embodiments, the methods further comprise performing biochemical methods capable of detecting structural differences of proteins. For example, proteolysis time point fractions can be combined with the metrics obtained from biophysical analysis on these fractions using, for example, mass spectrometry and activity assays.

In another embodiment of the invention, cellular levels of mRNA for a protein of interest may be tracked. The mRNA may be labelled in vitro or extracted and labelled. The labelled mRNA may be run on a gel to determine size or chemical modification. At the same time, phenotypic cell data such as cell size, motility, heat tolerance, or secreted protein levels may be measured. The relationship between mRNA expression level and phenotype may be captured by clustering the datapoints of size, chemical modification, and cellular activity. The method may be applied to larger systems such as in vivo models, using tissue sampling.

Implementation in a Computer System

The methods described may be implemented as computer programs that are executed on programmable computers comprising a processor and a data storage system. A computer program is a set of instructions that can be used, directly or indirectly, in a computer to perform a certain activity or to bring about a certain result. A computer program can be written in any form of programming language, including compiled or interpreted languages, and it can be deployed in any form, including as a stand-alone program or as a module, component, subroutine, function, procedure or other unit suitable for use in a computing environment.

The computer program can be stored on a computer-readable storage system. Examples of storage systems include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM.

A computer-readable storage system may be physically transformed such that it contains a computer program. It will be appreciated by one of skill in the art that a computer-readable storage system comprising instructions for performing any method disclosed herein is physically distinct from a computer-readable storage system that does not comprise such instructions. In other words, any given computer-readable storage system must be physically transformed to comprise instructions for performing any method disclosed herein. A computer-readable storage system comprising computer executable instructions, such as instructions for performing any method disclosed herein, is physically configured in such a manner so as to cause a computer interacting with the storage system to perform a process or a method. One of skill in the art will appreciate that a computer-readable storage system comprising computer executable instructions for performing any method disclosed herein, when accessed and read by a general purpose computer, will transform the general purpose computer into a special purpose computer.

Thus, in one aspect, the invention provides a computer-readable storage system comprising computer executable instructions for performing any method described herein. In one embodiment, a computer-readable storage system comprises computer executable instructions for clustering a first query datapoint to a first cluster comprising a first cluster center, wherein the first query datapoint and the first cluster center are selected from a plurality of datapoints in space and wherein each of the datapoints is characterized by a density, the clustering comprising (a) determining a first trace of the first query datapoint to the first cluster center, wherein the first trace comprises n datapoints selected from the plurality of datapoints and wherein n is an integer, the determining step comprising: (i) designating the first query datapoint as $x_1$; (ii) determining the remaining n−1 datapoints of the first trace, wherein the remaining n−1 datapoints are designated $x_2 \ldots x_n$; wherein $x_n$ designates the first cluster center; and wherein $x_{j+1}$ has the greatest density of all datapoints lying within a cutoff distance from $x_j$, wherein j is an integer selected from 1 to n−1; and (b) assigning the first query datapoint to the first cluster.

In a further aspect, the invention provides a computer system for performing any method described herein, the computer system comprising a data storage system and a processor comprising instructions for performing any method described herein. In one embodiment, a computer system for clustering a first query datapoint to a first cluster comprising a first cluster center, wherein the first query datapoint and the first cluster center are selected from a plurality of datapoints in space and wherein each of the datapoints is characterized by a density comprises (1) a data storage system and (2) a processor comprising instructions for performing a method comprising (a) determining a first trace of the first query datapoint to the first cluster center, wherein the first trace comprises n datapoints selected from the plurality of datapoints and wherein n is an integer, the determining step comprising: (i) designating the first query datapoint as $x_1$; (ii) determining the remaining n−1 datapoints of the first trace, wherein the remaining n−1 datapoints are designated $x_2 \ldots x_n$; wherein $x_n$ designates the first cluster center; and wherein $x_{j+1}$ has the greatest density of all datapoints lying within a cutoff distance from $x_j$, wherein j is an integer selected from 1 to n−1; and (b) assigning the first query datapoint to the first cluster.

It will be appreciated by one of skill in the art that a processor comprising instructions for performing any method disclosed herein is physically distinct from a processor that does not comprise such instructions. In other words, any given processor must be physically transformed to comprise instructions for performing any method disclosed herein.

The processor and the data storage system can be supplemented by or incorporated in application-specific integrated circuits (ASICs). When read into the processor of the computer, which is thus physically transformed, and executed or further processed before execution, the instructions of the program cause the programmable computer to carry out the various operations described herein. The processor and the data storage system are typically connected by a bus.

To provide for interaction with a user, the invention can be implemented on a computer comprising a display device such as, for example, a cathode ray tube (CRT) or liquid crystal display (LCD) monitor for displaying information to the user. The user can provide input, for example, via a keyboard, a touch screen or a pointing device such as a mouse or a trackpad. The various data generated by the present methods can be represented graphically using modeling and graphics software.

The different aspects and embodiments described herein can be implemented in a computer system that includes a backend component such as a data server, a middleware component such as an application server or an Internet server, or a front end component such as a client computer having a user interface, Internet browser or any combination thereof. The components of the system can be connected by any form or medium of digital data communication.

The present methods can be implemented on hardware in a variety of configurations. Thus, in some embodiments, computational processes are performed in parallel on nodes of a computer cluster, in a distributed computing system or on graphics processing units as these configurations are understood in the art.

Without intending to be limiting, the following examples are provided to give those of ordinary skill in the art a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for.

EXAMPLES

Example 1

Demonstration of the Method on a Simple Data Set

Figure 2:
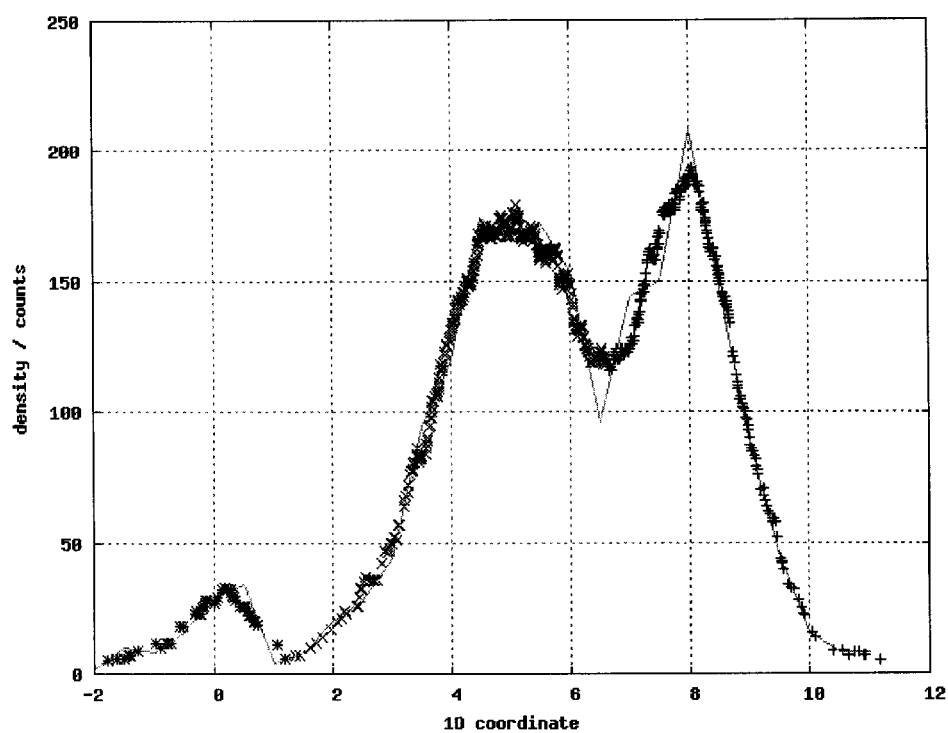
FIG. 2 shows a clustered one-dimensional data set. A cutoff parameter of 0.5 yields the following clustering along with a standard histogram (bin width=0.5) of the data. Symbols used to outline the clusters from left to right are *, x and +.

A one-dimensional data set that was generated by taking points at random from three superimposed Gaussian distributions is shown in FIG. 1. With a cutoff radius of 0.5, the correct clusters were recovered as confirmed by visual inspection in FIG. 2.

Example 2

Identifying the Different States of a Protein

Figure 3:
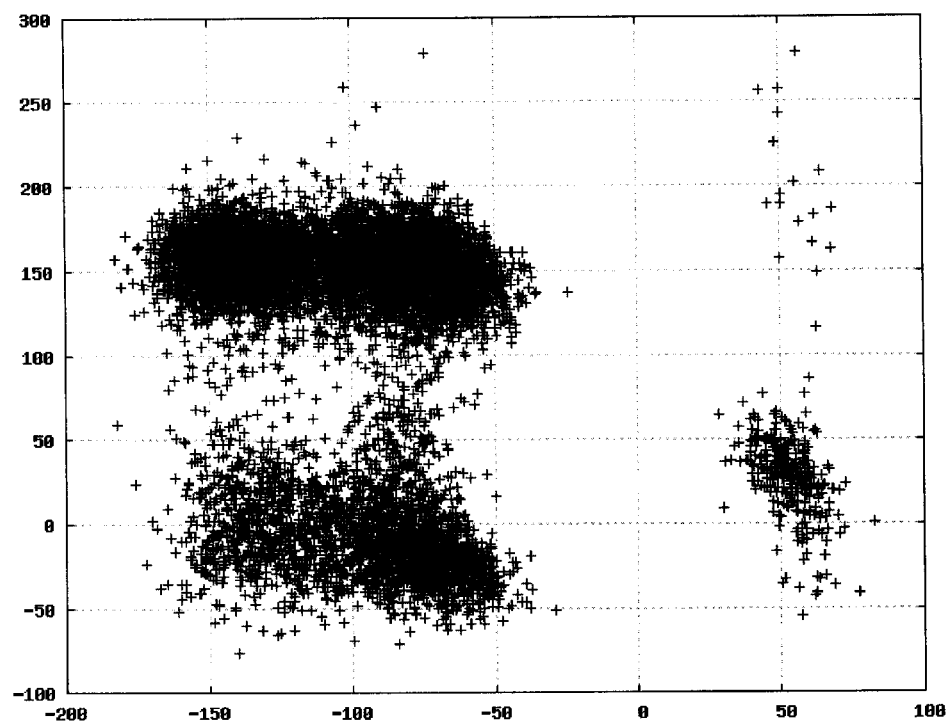
FIG. 3 depicts a two-dimensional data set in the form of a Ramachandran plot (phi/psi angles). Phi (x-axis) and psi (y-axis) angles were extracted from a long simulation of trialanine and displayed.
Figure 4:
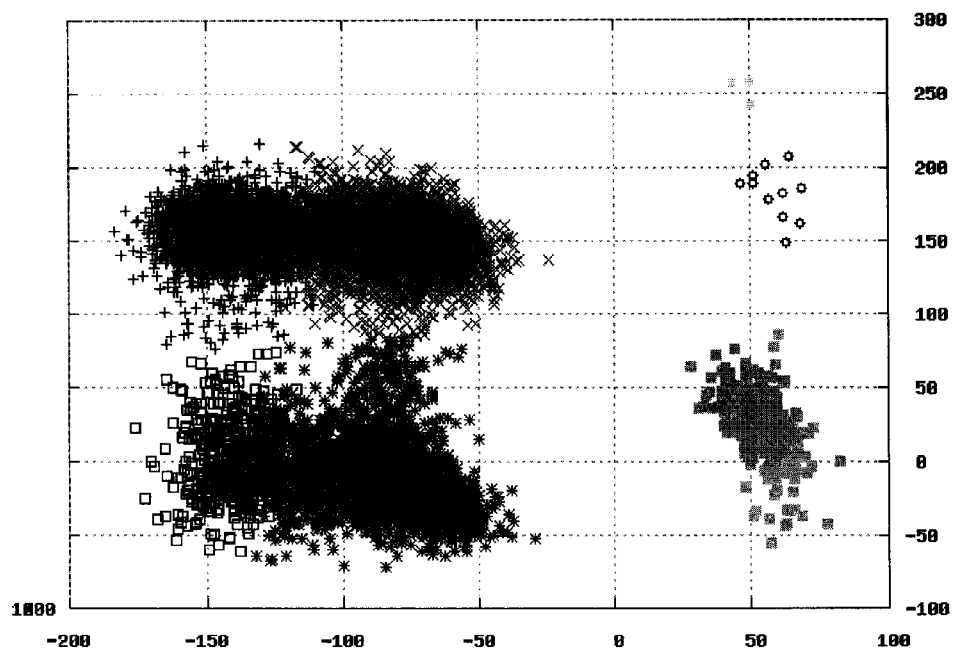
FIG. 4 depicts a two-dimensional data set clustered with a cutoff parameter of 15. The various clusters differ according to shading and symbol used to depict each point.
Figure 5:
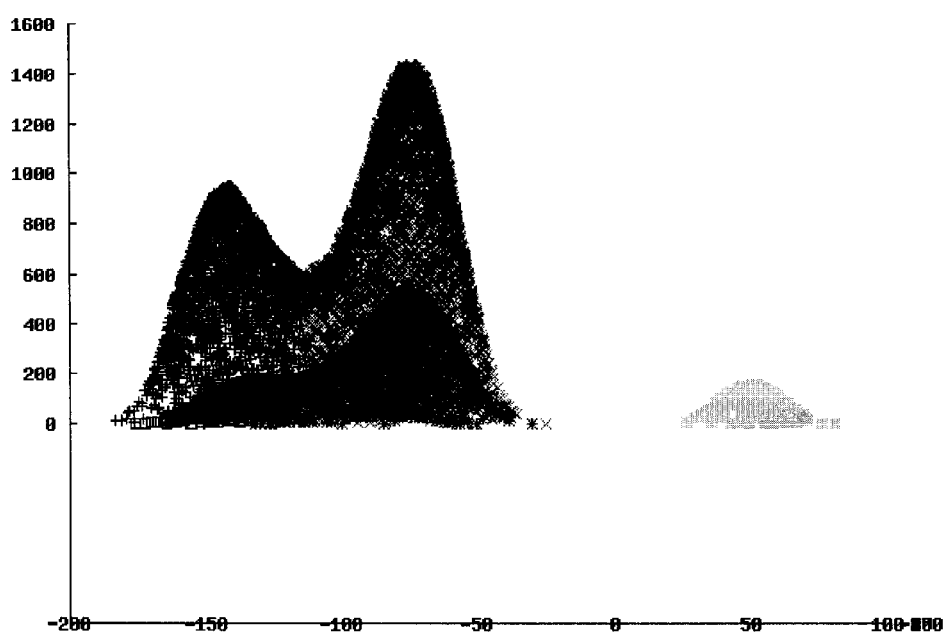
FIG. 5 shows a two-dimensional data set with the density of the points plotted against the phi and psi angles.

A Ramachandran plot distribution of phi/psi angles generated from a many nanosecond long computer simulation of trialanine is shown in FIG. 3. Applying the method of the invention to this two dimensional dataset yields the clustering result shown in FIG. 4 when using a preset cutoff of 15. A side view of the density of points vs. phi/psi angles (shaded by cluster) is shown in FIG. 5 and provides an illustration of the how the method of the invention may be applied.

Example 3

Identifying Different Conformations of a Protein at the Amino Acid Level

Figure 6:
FIG. 6 shows the clustering of conformations of a histidine residue. This is an 18-dimensional dataset (6 atoms, three coordinates each). The cutoff parameter used was 2.

The clustering results for the conformations of a single histidine molecule as observed in a 1 nanosecond trajectory is shown in FIG. 6. Simulation snapshots were aligned based on the protein backbone atoms (C, C$\alpha$, N) and clustered based on side chain heavy atom coordinates (x, y, z coordinates for each of 6 atoms—an 18-dimensional data set). The cutoff was set at 2. Two heavily populated clusters are clearly distinguished using the method of the invention.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

What is claimed is:

1. A computer system comprising a data storage system and a processor and further comprising instructions for performing a method of clustering a first query datapoint $x_1$ to a first cluster comprising a first cluster center, wherein the first query datapoint and the first cluster center are selected from a plurality of datapoints in space and wherein each of the datapoints is characterized by a density and wherein the plurality of datapoints further comprises datapoints assigned to one or more clusters other than the first cluster, the method comprising
  (a) determining a first trace of the first query datapoint to the first cluster center, wherein the first trace comprises n datapoints selected from the plurality of datapoints and wherein n is an integer, the determining step comprising:
    (i) identifying the first query datapoint $x_1$;
    (ii) determining the remaining n−1 datapoints $x_2 \ldots x_n$ of the first trace, wherein $x_n$ designates the first cluster center; and wherein $x_{j+1}$ has the greatest density of all datapoints lying within a cutoff distance from $x_j$, wherein j is an integer selected from 1 to n−1; and
  (b) assigning the first query datapoint to the first cluster, wherein the determining and the assigning are performed using the computer system.

2. The computer system of claim 1 wherein no point within the cutoff distance from the first cluster center is characterized by a density higher than the density of the first cluster center.

3. The computer system of claim 1 wherein $x_1 \ldots x_n$ are all assigned to the first cluster.

4. The computer system of claim 1 wherein the density of $x_j$ or $x_{j+1}$ is the number of all datapoints selected from the plurality of datapoints whose distance to $x_j$ or $x_{j+1}$, respectively, is less than or equal to the cutoff distance.

5. The computer system of claim 1 wherein $x_2$ is the first cluster center.

6. The computer system of claim 1 wherein the step of determining the remaining n−1 datapoints comprises determining a local density maximum neighbor of each of the datapoints of the first trace in sequence according to ascending index, wherein the local density maximum neighbor of $x_j$ is $x_{j+1}$.

7. The computer system of claim 1 wherein the density of $x_{j+1}$ is greater than the density of $x_j$.

8. The computer system of claim 1 wherein the step of determining the remaining n−1 datapoints of the first trace further comprises rejecting a rejected datapoint selected from the plurality of datapoints, wherein the density of one of the remaining n−1 datapoints $x_j$ and the density of the rejected datapoint are the same; wherein $x_j$ is characterized by a first global index, the rejected datapoint is characterized by a second global index and the first global index is greater than the second global index.

9. The computer system of claim 1 further comprising determining a second trace of a second query datapoint to the first cluster center; and assigning the second query datapoint to the first cluster.

10. The computer system of claim 9 further comprising assigning each datapoint of the second trace to the first cluster.

11. The computer system of claim 1 further comprising:
clustering a second query datapoint to a second cluster comprising a second cluster center;
numbering the first cluster; and
numbering the second cluster.

12. The computer system of claim 11 wherein the cluster numbering and datapoint assignments to the first cluster and the second cluster are visualized by a computer-generated graph.

13. The computer system of claim 11 wherein the first cluster and the second cluster are visualized in two or three dimensions.

14. The computer system of claim 1 wherein the cutoff distance is a single tunable parameter that affects the ability of the determining step (a) and the assigning step (b) to overcome one or more noisy points in the plurality of datapoints that are scattered between the first cluster and a second cluster.

15. The computer system of claim 1 wherein the plurality of datapoints exist in a dimensional space selected from the group consisting of one-, two-, or three dimensional space.

16. The computer system of claim 1 wherein the plurality of datapoints represent quantifiable phenomena selected from the group consisting of amino acid configurations, protein conformation coordinates, measurable differences between proteins, nucleic acid expression levels and phenotypic qualities.

17. The computer system method of claim 1 wherein the plurality of datapoints exist in a dimensional space that is greater than three dimensional space.

18. The computer system of claim 1, wherein n is an integer of 3 or greater.

19. A non-transitory computer readable medium comprising instructions for performing a method of clustering a first query datapoint $x_1$ to a first cluster comprising a first cluster center, wherein the first query datapoint and the first cluster center are selected from a plurality of datapoints in space and wherein each of the datapoints is characterized by a density and wherein the plurality of datapoints further comprises datapoints assigned to one or more clusters other than the first cluster, the method comprising
(a) determining a first trace of the first query datapoint to the first cluster center, wherein the first trace comprises n datapoints selected from the plurality of datapoints and wherein n is an integer, the determining step comprising:
(i) identifying the first query datapoint $x_1$;
(ii) determining the remaining n−1 datapoints $x_2 \ldots x_n$ of the first trace, wherein $x_n$ designates the first cluster center; and wherein $x_{j+1}$ has the greatest density of all datapoints lying within a cutoff distance from $x_j$, wherein j is an integer selected from 1 to n−1; and
(b) assigning the first query datapoint to the first cluster.

20. The non-transitory computer readable medium of claim 19, wherein n is an integer of 3 or greater.

\* \* \* \* \*